United States Patent [19]

Nanba et al.

[11] Patent Number: 5,309,776

[45] Date of Patent: May 10, 1994

[54] METHOD OF DIAGNOSING DETERIORATION OF INSULATING PAPER IN OIL-FILLED ELECTRIC APPARATUS

[75] Inventors: Sadao Nanba; Teruo Miyamoto, both of Ako, Japan

[73] Assignee: Mitsubishi Denki Kabushiki Kaisha, Tokyo, Japan

[21] Appl. No.: 818,875

[22] Filed: Jan. 10, 1992

[30] Foreign Application Priority Data

Jan. 14, 1991 [JP] Japan ................................. 3-2719

[51] Int. Cl.$^5$ ..................... G01N 33/34; G01M 19/00
[52] U.S. Cl. ...................................... 73/866; 73/865.9
[58] Field of Search ............................... 73/866, 865.9

[56] References Cited

FOREIGN PATENT DOCUMENTS

| | | | |
|---|---|---|---|
| 83-278 | 5/1983 | Japan | 73/866 |
| 173439 | 9/1985 | Japan | 73/866 |
| 235059 | 11/1985 | Japan . | |
| 250733 | 10/1989 | Japan | 73/866 |

OTHER PUBLICATIONS

Cigre Study Committee 15-WG 01, Paris 1986, "Monitoring of Power Transformers by HPLC Analysis"; F. Serena; 9 pages.

IEE Proceedings, vol. 132, Pt. C., No. 6, Nov. 1985; D. H. Schroff et al, pp. 312-319.

12-09 "Recent Developments by CEGB to Improve the Prediction and Monitoring of Transformer Performance", 1984; P. J. Burton et al. pp. 1-10.

CA 104(20): 171 250 b 1992 copyright ACC, English Abstract of Japan 60-235059.

*Primary Examiner*—Tom Noland
*Attorney, Agent, or Firm*—Sughrue, Mion, Zinn, Macpeak and Seas

[57] ABSTRACT

In a method of diagnosing the deterioration of the insulating paper in an oil-filled electric apparatus, the total amount of furfural is determined by adding the amount of furfural adsorbed on the insulating paper to the amount of furfural dissolved in insulating oil in an oil-filled electric apparatus, and the deterioration of the insulating paper is diagnosed by the correlation between the total amount of furfural determined and the polymerization degree of the insulating paper, which indicates the degree of deterioration thereof. The method thus permits the precise diagnosis of the deterioration of the insulating paper.

3 Claims, 1 Drawing Sheet

METHOD OF DIAGNOSING DETERIORATION OF INSULATING PAPER IN OIL-FILLED ELECTRIC APPARATUS

BACKGROUND OF THE INVENTION

1. Field of the Invention

The present invention relates to a method of diagnosing the deterioration of insulating paper used in an oil-filled electric apparatus such as an oil-filled transformer, an oil-filled reactor or the like.

2. Description of Related Art

The life of an oil-filled electric apparatus such as an oil-filled transformer, an oil-filled reactor or the like is generally estimated from the degree of deterioration of the insulating paper used therein. The degree of deterioration of the insulating paper is determined by measuring its tensile strength, the degree of polymerization thereof and the like. Investigation is increasingly made as to whether or not deterioration of such insulating paper can be diagnosed by measuring the deterioration products, ex. furans such as furfural, furancarboxylic acid and the like, and aldehydes such as acetoaldehyde, formaldehyde and the like.

However, the measurement of the degree of deterioration of insulating paper by measuring its tensile strength and the degree of polymerization thereof is limited to the opportunity for internal inspection which allows the insulating paper to be collected from an oil-filled electric apparatus. On the other hand, as the insulating paper decomposes, furfural (also referred to as furaldehyde) is produced and dissolves in insulating oil. Since the amount of furfural dissolved in the insulating oil can be measured by collecting the insulating oil, there is the advantage that the life of the oil-filled electric apparatus can be diagnosed during the operation thereof. However, it has become clear that the furfural produced from the insulating paper used in the oil-filled electric apparatus not only dissolves in the insulating oil but also is well adsorbed on the insulating paper, as described below. This led to the finding that the total amount of furfural cannot be measured by analyzing only the furfural dissolved in the insulating oil.

Since this finding has previously not been taken into account, there has been the following problem: If the degree of deterioration of insulating paper is diagnosed from the analytical result of furfural dissolved in insulating oil, the calculated amount of furfural produced is smaller than the actual furfural amount by the amount of furfural adsorbed on the insulating paper. This results in poor precision of diagnosis of the life of the apparatus.

SUMMARY OF THE INVENTION

The present invention has been developed for solving the above problem, and it is an object of the invention to precisely diagnose the deterioration of the insulating paper used in an oil-filled electric apparatus from the total of the amount of furfural dissolved in insulating oil and the amount of furfural adsorbed on the insulating paper.

In order to achieve the object, the present invention provides a method of diagnosing the deterioration of the insulating paper in an oil-filled electric apparatus comprising the steps of determining the amount of furfural adsorbed on the insulating paper in the oil-filled electric apparatus, determining the total amount of furfural by adding the amount of furfural dissolved in insulating oil to the amount of furfural adsorbed, calculating the furfural production per gram of insulating paper from the total amount of furfural and the amount of insulating paper in the highest-temperature portion of the oil-filled electric apparatus, and determining the degree of residual polymerization of the insulating paper from a previously obtained relationship between the furfural production and the degree of residual polymerization of the insulating paper, to diagnose the degree of deterioration of the insulating paper.

In the present invention, the amount of furfural adsorbed on the insulating paper of an oil-filled electric apparatus is determined by determining the equilibrium concentration of furfural adsorbed on the insulating paper using a measurement tank containing the insulating paper of the oil-filled electric apparatus and the insulating oil thereof, and the total amount of furfural produced from the insulating paper is determined by adding the amount of furfural adsorbed on the insulating paper to the amount of furfural dissolved in the insulating oil, whereby the deterioration of the insulating paper can be diagnosed by the relationship between the total amount of furfural and the polymerization degree of the insulating paper which indicates the degree of deterioration thereof.

DETAILED DESCRIPTION OF PREFERRED EMBODIMENTS

An embodiment of the present invention is described below with reference to the drawings.

Insulating oil in which a predetermined amount of furfural was dissolved and insulating paper were placed in a measurement tank (not shown), and then heated at a predetermined temperature of 55° to 100° C. A portion of the insulating oil was then collected from the measurement tank in the course of heating, and furfural was analyzed by liquid chromatography.

Figure 1:
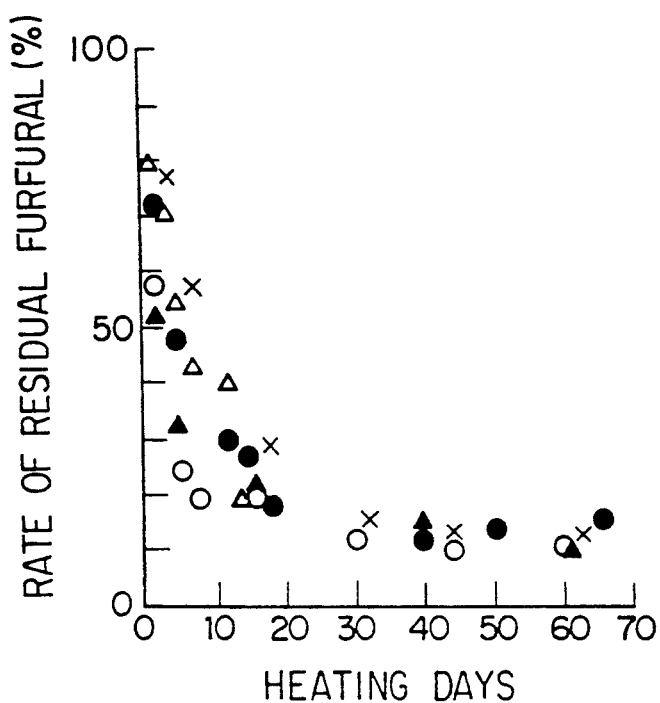
FIG. 1 is a graph showing a relation between the number of days for heating a measurement tank and the amount of furfural remaining in oil.

FIG. 1 is a graph showing the relation between the rate or percentage of furfural remaining in the insulating oil and the heating days on the assumption that the initial furfural concentration is 100. In the graph, marks ●, ○, △ and x show the results of heating at 100° C., 85° C., 70° C. and 55° C., respectively, at an initial furfural concentration of 2 ppm, and ▲ shows the results of heating at 85° C. and an initial furfural concentration of 20 ppm. As seen from the graph, the amount of furfural dissolved in the oil deceases due to the adsorption on the insulating paper. Since furfural is an intermediate produced in the process of deterioration, it is estimated that furfural has no thermal stability. Changes of insulating oil containing furfural with the passage of time were also measured during heating at 100° C. As a result, the amount of furfural dissolved in the oil was substantially the same as the initial value after two months had passed, and furancarboxylic acid, which was produced by oxidation of furfural, was not detected. It is therefore thought that the data with respect to convergence of the furfural concentration to about 15% is based on the phenomenon caused by adsorption of furfural on the insulating paper.

In this embodiment, the process of adsorption of furfural contained in the insulating oil on the insulating paper is investigated by the amount of furfural remaining in the oil. The adsorption equilibrium is thus determined from the process opposite to the process in an actual transformer. In the investigation, the ratio between the insulating oil and the insulating paper was equivalent to that in an actual transformer.

The constant concentration after the passage of heating days is the adsorption equilibrium concentration. It was found that the amount of remaining furfural which reaches the adsorption equilibrium concentration depends upon neither the temperature nor the initial concentration, but it converges to about 15%. Namely, this finding shows that the adsorption equilibrium concentration of furfural is about 15% of the initial concentration. The total amount of furfural produced can thus be determined by multiplying the amount of furfural dissolved in the oil by 6.7 (100/15=6.7).

Figure 2:
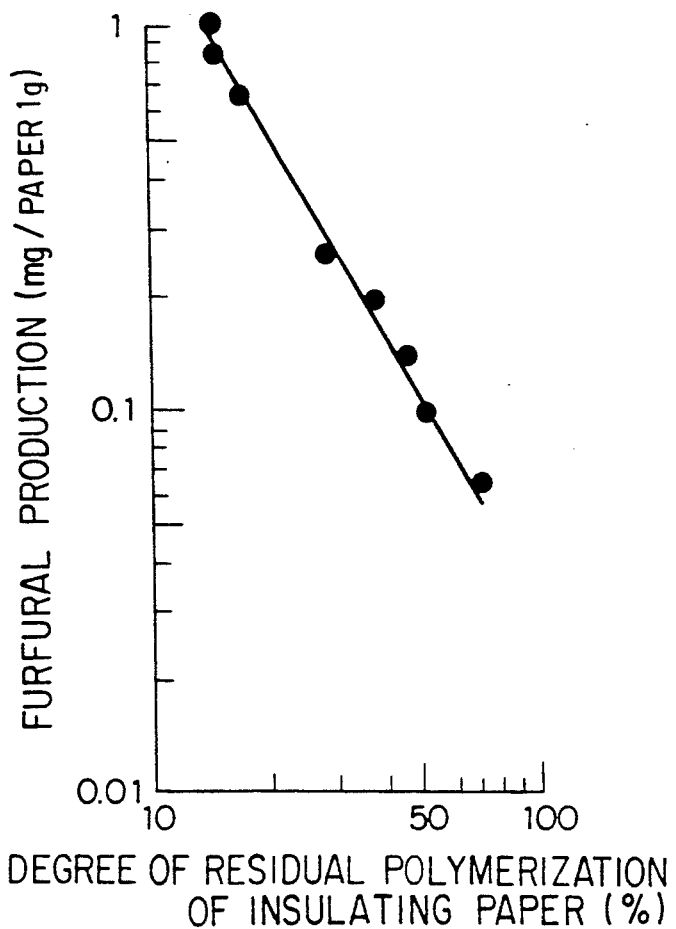
FIG. 2 is a graph showing a relation between the degree of residual polymerization of insulating paper and the amount of furfural produced.

FIG. 2 shows the relation between the furfural production and the degree of residual polymerization of insulating paper. The furfural production and the polymerization degree of insulating paper, which indicates the degree of deterioration thereof, have a good correlation therebetween. In order to diagnose the deterioration of the insulating paper used in an oil-filled electric apparatus, the total amount of furfural produced is first determined by adding the amount of furfural adsorbed on the insulating paper to the amount of furfural dissolved in the insulating oil. The furfural production per gram of insulating paper is then calculated from the total amount of furfural and the amount of the insulating paper in the highest-temperature portion of the oil-filled electric apparatus. The degree of residual polymerization is then determined from the graph shown in FIG. 2, whereby the degree of deterioration of the insulating paper can be diagnosed. The above-described method permits the precise determination of the degree of deterioration of the insulating paper.

What is claimed is:

1. A method of diagnosing the deterioration of insulating paper in an insulating oil-filled electric apparatus, comprising the steps of:
   a) determining the amount of furfural dissolved in the insulating oil;
   b) determining the amount of furfural adsorbed on the insulating paper in the oil-filled electric apparatus;
   c) determining the total amount of furfural by adding the amount of dissolved furfural to the amount of adsorbed furfural;
   d) calculating the furfural production per gram of insulating paper from said total amount of furfural and the amount of the insulating paper in a highest-temperature portion of said oil-filled electric apparatus; and
   e) determining the degree of residual polymerization of said insulating paper from a previously obtained relationship between furfural production and the degree of residual polymerization of said insulating paper, so as to diagnose the degree of deterioration of said insulating paper.

2. A method according to claim 1 wherein said total amount of furfural is determined from the equilibrium concentration of furfural adsorbed on said insulating paper which is obtained by measuring heat induced changes of an initial dissolved furfural concentration with time.

3. A method according to claim 2 wherein said equilibrium concentration of furfural adsorbed on said insulating paper is about 15% of the initial concentration.

* * * * *